United States Patent
Cheng et al.

(10) Patent No.: US 10,515,790 B2
(45) Date of Patent: Dec. 24, 2019

(54) ION GUIDING DEVICE

(71) Applicant: SHIMADZU CORPORATION, Kyoto-shi, Kyoto (JP)

(72) Inventors: Yupeng Cheng, Shanghai (CN); Xiaoqiang Zhang, Shanghai (CN); Wenjian Sun, Shanghai (CN)

(73) Assignee: SHIMADZU CORPORATION, Kyoto-Shi, Kyoto (JP)

( * ) Notice: Subject to any disclaimer, the term of this patent is extended or adjusted under 35 U.S.C. 154(b) by 0 days.

(21) Appl. No.: 15/736,107

(22) PCT Filed: Jun. 20, 2016

(86) PCT No.: PCT/JP2016/002947
§ 371 (c)(1),
(2) Date: Dec. 13, 2017

(87) PCT Pub. No.: WO2017/013832
PCT Pub. Date: Jan. 26, 2017

(65) Prior Publication Data
US 2018/0174812 A1 Jun. 21, 2018

(30) Foreign Application Priority Data
Jul. 23, 2015 (CN) .......................... 2015 1 0437333

(51) Int. Cl.
*H01J 49/38* (2006.01)
*H01J 49/06* (2006.01)
(Continued)

(52) U.S. Cl.
CPC .......... *H01J 49/066* (2013.01); *G01N 27/622* (2013.01); *H01J 49/40* (2013.01); *H01J 49/4205* (2013.01)

(58) Field of Classification Search
USPC ........................................................ 250/283
See application file for complete search history.

(56) References Cited

U.S. PATENT DOCUMENTS

| 5,847,386 A | 12/1998 | Thomson et al. |
| 6,107,628 A | 8/2000 | Smith et al. |

(Continued)

FOREIGN PATENT DOCUMENTS

| CN | 101416271 A | 4/2009 |
| JP | 2008-530748 A | 8/2008 |

(Continued)

OTHER PUBLICATIONS

International Search Report (ISR) issued by the European Patent Office (EPO) dated Sep. 20, 2016 for PCT/JP2016/002947.
(Continued)

*Primary Examiner* — Phillip A Johnston
(74) *Attorney, Agent, or Firm* — Tim Tingkang Xia, Esq.; Locke Lorde LLP

(57) ABSTRACT

The disclosure relates to an ion guiding device, including two sets of electrodes extending along a certain space axis, a first power supply device and a second power supply device. The electrodes are expandably arranged along a direction perpendicular to the space axis, at least one surface of each electrode in each set of electrodes is substantially on the same space plane, and the space planes for each set of electrodes are not same and not parallel, thereby forming an ion transmission channel having the cross sectional area gradually reduced in a direction perpendicular to the space axis; the first power supply device is used for applying radio-frequency voltages on at least a part of electrodes in the two sets of electrodes; and the second power supply device is used for applying voltage signals on at least a part of electrodes in the two sets of electrodes.

24 Claims, 13 Drawing Sheets

(51) Int. Cl.
  *G01N 27/62*    (2006.01)
  *H01J 49/40*    (2006.01)
  *H01J 49/42*    (2006.01)

(56) References Cited

U.S. PATENT DOCUMENTS

| | | | |
|---|---|---|---|
| 6,891,157 B2 | 5/2005 | Bateman et al. | |
| 7,868,289 B2* | 1/2011 | Cousins | H01J 49/063 |
| | | | 250/281 |
| 8,067,747 B2* | 11/2011 | Wollnik | H01J 49/062 |
| | | | 250/281 |
| 8,193,489 B2 | 6/2012 | Bertsch et al. | |
| 8,299,443 B1 | 10/2012 | Shvartsburg et al. | |
| 8,835,839 B1 | 9/2014 | Anderson et al. | |
| 9,147,567 B2* | 9/2015 | Loboda | H01J 49/4255 |
| 9,613,788 B2* | 4/2017 | Welkie | H01J 49/062 |
| 9,786,485 B2* | 10/2017 | Ding | H01J 49/067 |
| 2004/0222369 A1 | 11/2004 | Makarov et al. | |
| 2008/0210859 A1 | 9/2008 | Tolley et al. | |
| 2009/0206250 A1* | 8/2009 | Wollnik | G01N 27/622 |
| | | | 250/290 |
| 2013/0187044 A1 | 7/2013 | Ding et al. | |
| 2014/0084156 A1 | 3/2014 | Ristroph et al. | |
| 2014/0217275 A1 | 8/2014 | Ding et al. | |
| 2017/0263429 A1* | 9/2017 | Dominguez | H01J 49/063 |

FOREIGN PATENT DOCUMENTS

| | | |
|---|---|---|
| JP | 2009-538501 A | 11/2009 |
| WO | 2012120297 A1 | 9/2012 |
| WO | 2013027054 A2 | 2/2013 |
| WO | 2013027055 A1 | 2/2013 |

OTHER PUBLICATIONS

Austin, Daniel E. et al., "Halo Ion Trap Mass Spectrometer", Analytical Chemistry, vol. 79, Issue 7, pp. 2927-2932, Apr. 1, 2007.

Japan Patent Office, "JP Office Action for JP Application No. JP2017-565874", Japan, dated Nov. 12, 2018.

* cited by examiner

ION GUIDING DEVICE

FIELD OF THE INVENTION

The present invention relates to an ion guiding device, and particularly to an ion guiding device for axially driving ions using penetration voltage.

BACKGROUND OF THE INVENTION

As is well known, an ion guiding device is an indispensable key component for a mass spectrometer, and the performance of the ion guiding device greatly affects the whole mass spectrometer in terms of many properties such as sensitivity, mass range and scanning speed. In view of various ion guiding devices used in the current main commercial mass spectrometers, a quadrupole rod and a multipole rod (generally, a hexapole rod or an octupole rod) typically are the most common structures. As an ion guiding device, a quadrupole rod has the advantage of better ion beam compression effects, thus facilitating efficient introduction of ions to a next-stage ion optical device. However, a quadrupole rod has a smaller ion acceptance area and a lower ion transmission efficiency when compared with a multipole rod. Additionally, a quadrupole rod and a multipole rod generally have a low operating gas pressure to ensure that an RF field generated by a radio-frequency voltage can effectively confine ions. Meanwhile, the axial transmission of ions can be achieved only by initial kinetic energy or gas flow driving due to the absence of an axial driving electric field, thus the ions can dwell therein for a relatively longer period of time, which affects the analysis speed of an instrument.

In an U.S. Pat. No. 6,107,628, Richard D. Smith et al. disclose an ion funnel technique, wherein a series of ring electrodes with inner diameters gradually reduced are used and then stacked in an axial direction to form a funnel structure with a tapered opening. Because radio-frequency voltages of opposite phases are applied among adjacent ring electrodes and the electrodes are in series connection via resistors to form an axial voltage dividing structure, a radial multipole field and a axial electric field are formed in the ion funnel structure to achieve axial transmission and radial compression of ions. The apparatus has the advantages of the ion compression function of a quadrupole rod and the large ion acceptance area and high ion transmission efficiency of a multipole rod, and can operate at an extremely high gas pressure. However, this technical solution employs an stacked structure of the ring electrodes such that the electrodes are segmented axially, thus an axial voltage dividing design is required to achieve the axial driving of ions, resulting in that the apparatus has a relatively complicated structure and circuit connection and cannot be conveniently machined. Additionally, the apparatus has a poor resistance to sample contamination.

In another U.S. Pat. No. 8,299,443B1, Alexander A. Shvartsburg et al. propose a planar ion funnel device, wherein a planar structure design as well as an extremely small electrode size and electrode gap (<200 um) are employed based on the above ion funnel device to increase the operating gas pressure and discharge voltage of the ion funnel. However, the basic operating principle and design concept of this planar ion funnel device are not greatly different from those of the above ion funnel device.

Additionally, in an U.S. Pat. No. 8,835,839B1, Gordon A. Anderson et al. propose a structure for lossless ion manipulation, wherein the structure consists of electrode arrays adhered on two surfaces, thus various ion manipulations can be achieved in the structure by applying RF voltage and DC voltage. The flexible expansibility of the structure greatly depends on a set of parallel planar electrode structures. Additionally, it is difficult for the structure to achieve the ion compression effects.

In an U.S. Pat. No. 5,847,386, Bruce A. Thomson et al. propose an ion guiding structure consisting of rod electrodes, wherein an axial driving electric field is established by changing the cross section area of the rod electrodes and the head-to-tail spacing between the rod electrodes, and also propose the use of auxiliary electrodes to adjust the axial electric potential distribution. However, in the structure, the establishment of the axial driving electric field requires a change in the section of the rod electrodes, and involves changing the head-to-tail spacing between the rod electrodes in two directions, i.e. an inlet section and an outlet section forming the structure are both changed in two directions, and the structure additionally depends on the auxiliary electrodes, which causes this structure to be relatively complicated.

Similarly, in another U.S. Pat. No. 7,868,289B2, Lisa Cousins et al. propose an ion guiding device consisting of parallel rod electrodes with rectangular cross-sections, wherein the cross-sections of the rod electrodes are gradually reduced along the length thereof, and the ion guiding device is surrounded by an additional cylindrical electrode, thus establishing an axial driving electric field. Likewise, the structure is relatively complicated and depends on the cylindrical electrode.

Additionally, in an U.S. Pat. No. 8,193,489B2, James L. Bertsch et al. propose an ion guiding and compression device which allows a multipole rod to be gradually evolved into a plurality of quadrupole rods, but, in the device, it is necessary to apply a DC voltage drop along a length direction thereof onto rod electrodes so as to establish an axial driving electric field.

Meanwhile, in an U.S. Pat. No. 6,891,157B2, Robert Harold Bateman et al. also propose an ion transmission structure consisting of plate electrodes placed on a plane. The device is characterized in that a complicated ion transmission path can be achieved by combining different plate electrodes, thus reducing the noise resulting from neutral molecules. However, a concept is not provided in this patent that an penetration voltage gradient is produced in an axial direction by applying a voltage gradient in a direction perpendicular to the axial direction so as to drive axial transmission of ions. Additionally, the device is also limited in that the device greatly depends on plate electrodes, thus a larger capacitance occurs between the electrodes of the device, which causes a greater power consumption when ions are confined using a RF power source.

In summary, the electrode structures and circuit connections in the existing ion guiding and compression techniques are relatively complicated and cannot be conveniently machined. Accordingly, it is currently a research subject of intense interest to use a simple structure to achieve highly efficient ion transmission and compression.

SUMMARY OF THE INVENTION

In view of the above disadvantages in the prior art, an object of the present invention is to provide an ion guiding device, which comprises an ion channel consisting of two sets of electrode systems extending along a certain space axis, wherein the ion channel has a cross sectional area gradually reduced axially in a plane perpendicular to the axis, and a voltage gradient is applied in a direction perpendicular to the axis to produce an axial voltage gradient to realize axial transmission of ions; and the ion guiding device is simple in electrode shape and in structure, can be conveniently machined, assembled and expanded in function, and can realize efficient transmission and effective compression of ions.

To achieve the above and other relevant objects, the present invention provides an ion guiding device, which comprises two sets of electrodes extending along a certain space axis, a first power supply device and a second power supply device; wherein the two sets of electrodes are expandably arranged along a direction perpendicular to the space axis, at least one surface of each electrode in each set of electrodes is substantially on the same space plane, and the space planes for each set of electrodes are not same and not parallel, thereby forming an ion transmission channel having a cross sectional area gradually reduced in a direction perpendicular to the space axis; the ion inlet of the ion transmission channel has a larger opening and the ion outlet thereof has a smaller opening; the first power supply device is used for applying radio-frequency voltages on at least a part of electrodes in the two sets of electrodes to confine ions in the ion transmission channel in at least one direction perpendicular to the space axis; and the second power supply device is used for applying voltage signals on at least a part of electrodes in the two sets of electrodes to form a voltage distribution in at least one direction perpendicular to the space axis to control ion movement, and form a voltage distribution in a direction of the space axis to realize ion transmission along the space axis.

In the ion guiding device described above, the space axis is a linear or curved axis. Further, in the ion guiding device described above, when the space axis is a curved axis, an axial direction at the ion inlet is a first axial direction, an axial direction at the ion outlet is a second axial direction, and an included angle between the first axial direction and the second axial direction is one of less than 10°, 10°-20°, 20°-30°, 30°-40°, 40°-50°, 50°-60°, 60°- 70°, 70°-80°, 80°-90°, 90°-100°, 100°-110°, 110°-120°, 120°-130°, 130°-140°, 140°-150°, 150°-160°, 160°-170° and 170°-180°.

In the ion guiding device described above, electrodes in the two sets of plate electrodes are plate or nonplanar electrodes.

In the ion guiding device described above, the plate electrodes comprise one or a combination of square-pole electrodes, rectangular plate electrodes, fan-shaped plate electrodes, and thin-layer plate electrodes adhered on an insulating substrate.

Still further, in the ion guiding device described above, the insulating substrate is one of a printed circuit board, polyimide, ceramics and glass.

Further, in the ion guiding device described above, the nonplanar electrodes are electrodes whose surfaces are partially or all nonplanar.

In the ion guiding device described above, the space plane is planar and/or nonplanar.

In the ion guiding device described above, an area ratio of the ion inlet to the ion outlet is one of 1-10, 10-100, 100-1,000 and more than 1,000.

In the ion guiding device described above, the first power supply device sequentially applies radio-frequency voltages with opposite polarity to all electrodes in each set of electrodes.

In the ion guiding device described above, voltage signals applied by the second power supply device are selected from one or a combination of DC voltages, square wave voltages, sawtooth wave voltages, triangle wave voltages and AC voltages.

Further, in the ion guiding device described above, a duty cycle of the square wave voltages is in the range of one or more of 0-10%, 10%-20%, 20%-40%, 40%-60% and 60%-100%.

Further, in the ion guiding device described above, the AC voltage signals have a frequency of 10 Hz-100 MHz.

In the ion guiding device described above, the expandable arrangement of the two sets of electrodes in a direction perpendicular to the space axis is parallel and/or non-parallel expanded arrangement.

In the ion guiding device described above, none of electrodes in the two sets of electrodes is segmented axially.

The ion guiding device described above further comprises auxiliary electrodes, wherein the auxiliary electrodes are placed at both sides of the ion guiding device, and the second power supply device applies voltage signals to the auxiliary electrodes to restrict ion movement in a direction perpendicular to the space axis and produce an axial voltage gradient in the ion channel to realize ion transmission.

Further, in the ion guiding device described above, the auxiliary electrodes are parallel or not parallel to the space axis.

Further, in the ion guiding device described above, the auxiliary electrodes are planar or nonplanar electrodes.

In the ion guiding device described above, the operating gas pressure of the ion guiding device is in the range of one or more of $2\times10^5$ Pa-$2\times10^3$ Pa, $2\times10^3$ Pa-20 Pa, 20 Pa –2Pa, 2 Pa-$2\times10^{-1}$ Pa, $2\times10^{-1}$ Pa-$2\times10^{-3}$ Pa and less than $2\times10^{-3}$ Pa.

In the ion guiding device described above, the optimal operating gas pressure of the ion guiding device is in the range of 0.1 Pa-100 Pa.

In the ion guiding device described above, the two sets of electrodes expand along a direction perpendicular to the space axis to form an array structure.

In the ion guiding device described above, the two sets of electrode systems expand along a certain closed curve to form a closed array structure.

The ion guiding device described above comprises a plurality of ion injection ports for injecting ions into the ion inlet.

Further, in the ion guiding device described above, the ion injection direction is one or a combination of a direction of the space axis and a direction perpendicular to the space axis.

In the ion guiding device described above, the ion guiding device serves as one or a combination of a preceding-stage ion guiding device, an ion mobility analysis device, an ion compression device, an ion storage device, a collision chamber and an ion buncher device of a mass spectrometer or an ion mobility spectrometer.

As described above, the ion guiding device of the present invention has the following beneficial effects:

(1) the electrode shape and the device structure are simple, thereby facilitating machining, assembling and function expansion;

(2) high efficient transmission and effective compression of ions can be realized;

(3) the device can be applied to relevant technical fields such as mass spectrometry and ion mobility spectrometry;

(4) the device can be applied to ion beam compression in an orthogonal-injection ion time-of-flight mass spectrometer, wherein ions are efficiently compressed to reduce the initial spatial distribution of the ions, thereby improving the resolution of the instrument; and (5) in triple quadrupole mass spectrometers and other mass spectrometers, the device can conveniently realize off-axis ion optical design, which not only can effectively reduce the interference from neutral gas molecules and improve the signal-to-noise ratio of the instrument, but also can greatly reduce the volume of the instrument.

DESCRIPTION OF REFERENCE NUMERALS OF ELEMENTS IS AS FOLLOWS

Figure 1:
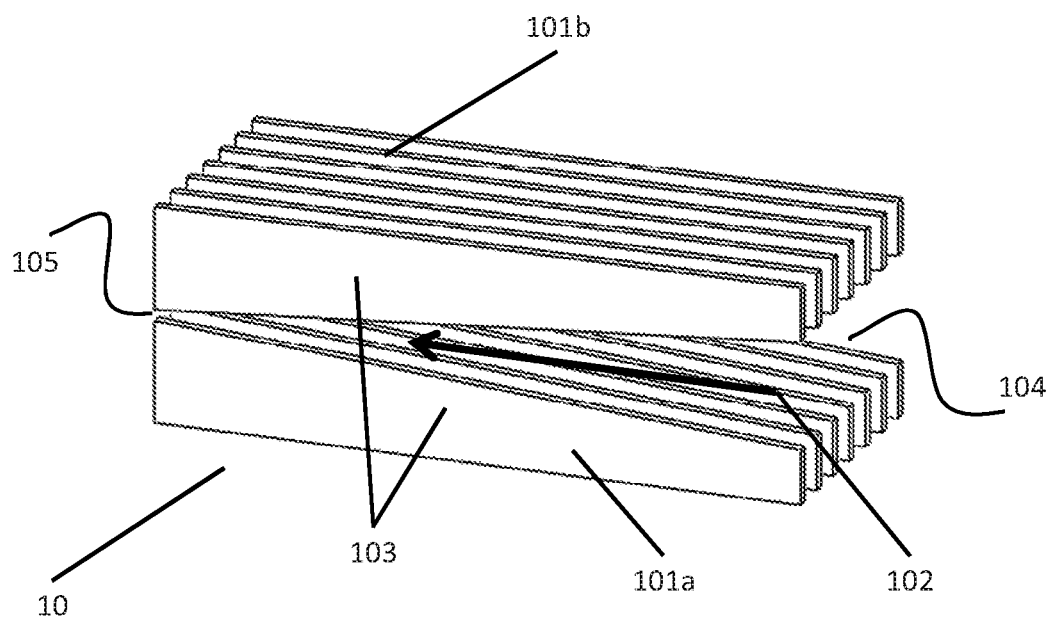
FIG. 1 shows a schematic structural view of the most preferred embodiment of the ion guiding device of the present invention.

10 Ion guiding device
101a Plate electrode
101b Plate electrode
102 Space axis
103 Electrode
104 Ion inlet
105 Ion outlet
106 Slit
107 Detector
108 Auxiliary electrode
400 Array electrode structure
401 Ion injection port
402 Ion stream
403 Ion outlet channel
404 Ion storage area
410 Closed electrode structure

DETAILED DESCRIPTION OF THE INVENTION

The embodiments of the present invention will be described hereinafter through specific particular examples, and those skilled in the art can easily understand other advantages and effects of the present invention through the disclosures in the specification. The present invention may also be implemented or applied through other different particular embodiments, and various modifications or changes may also be made to various details in the specification on the basis of different opinions and applications without departing from the spirit of the present invention.

It should be noted that the drawings provided in the embodiment only describe the basic conception of the present invention in an illustrative manner, so the drawings only show the components relevant to the present invention rather than being drawn according to the number, shape and size of the components during actual implementation, the configuration, number and scale of each component may be randomly changed during its actual implementation, and the layout and configuration of the components thereof might also be more complicated.

The ion guiding device of the present invention is an ion guiding device and an ion mobility analysis device for performing operations such as transmission, compression, splitting and collision-induced dissociation of an ion stream, and can be used in ion analyzers such as a mass spectrometer and an ion mobility spectrometer.

Particularly, the ion guiding device of the present invention comprises an ion channel consisting of two sets of electrode systems extending along a certain space axis, wherein the ion channel has a sectional area gradually reduced axially in a direction perpendicular to an axis; and a voltage gradient is applied in a direction perpendicular to the axis to produce an axial voltage gradient to drive axial transmission of ions. In the ion guiding device, electrodes do not need to be segmented axially, which is very favorable for machining and assembling while reducing the complexity of circuit design; and an ion inlet is large and an ion outlet is small, which not only ensures a larger ion acceptance area, but also may realize excellent ion compression effect. Accordingly, the ion guiding device of the present invention can be used in a mass spectrometer, an ion mobility spectrometer and a combination thereof to realize uses such as transmission and collision-induced dissociation of ions as well as compression and splitting of ion stream.

Embodiment 1

FIG. 1 shows a schematic structural view of the most preferred embodiment of the ion guiding device of the present invention. As shown, the ion guiding device 10 comprises two sets of plate electrodes 101a and 101b extending along a space axis 102, the first power supply device and the second power supply device. The two sets of plate electrodes 101a and 101b are expandably arranged along a direction perpendicular to the space axis 102, at least one surface of each electrode 103 in each set of plate electrodes is substantially on the same space plane, and the space planes for each set of plate electrodes 101a and 101b are not same and not parallel, i.e. an included angle between the two space planes is not 180°, thereby forming an ion transmission channel having cross sectional area gradually reduced in a direction perpendicular to the space axis 102. An ion inlet 104 of the ion transmission channel has a larger opening and an ion outlet 105 thereof has a smaller opening. It should be noted that, the most preferred embodiment of the present invention is that at least one surface of each electrode 103 in each set of plate electrodes is on the same space plane. However, on such basis, it also falls within the protection scope of the present invention that at least one surface of each electrode 103 in each set of plate electrodes is on the same space plane within a certain slight error range.

The first power supply device is used for applying radio-frequency voltages on at least a part of electrodes in the two sets of plate electrodes to confine ions in the ion transmission channel in at least one direction perpendicular to the space axis 102.

The second power supply device is used for applying voltage signals on at least a part of electrodes in the two sets of plate electrodes to form a voltage distribution in at least one direction perpendicular to the space axis 102 to control ion movement; and meanwhile, since the ion transmission channel has a cross sectional area gradually reduced along the space axis in a direction perpendicular to the space axis, a voltage distribution in a direction perpendicular to the space axis 102 forms a certain voltage distribution in a direction of the space axis 102, thus ion transmission can be realized along the space axis.

Preferably, the space plane is planar and/or nonplanar.

Preferably, an area ratio of the ion inlet to the ion outlet may be selected from the following: a) 1-10; b) 10-100; c) 100-1,000; and d) >1,000.

Preferably, voltage signals applied by the second power supply device are selected from one or a combination of DC voltages, square wave voltages, sawtooth wave voltages, triangle wave voltages and AC voltages. A duty cycle of the square wave voltages is adjustable and selected from at least one of the following ranges: a) 0-10%; b) 10%-20%; c) 20%-40%; d) 40%-60%; and e) 60%-100%. The AC voltage signals have a frequency of 10 Hz-100 MHz.

Preferably, all electrodes in the two sets of electrodes are not segmented axially.

Preferably, the ion guiding device serves as one or a combination of a preceding-stage ion guiding device, an ion mobility analysis device, an ion compression device, an ion storage device, a collision chamber and an ion buncher device of a mass spectrometer or an ion mobility spectrometer.

Figure 2:
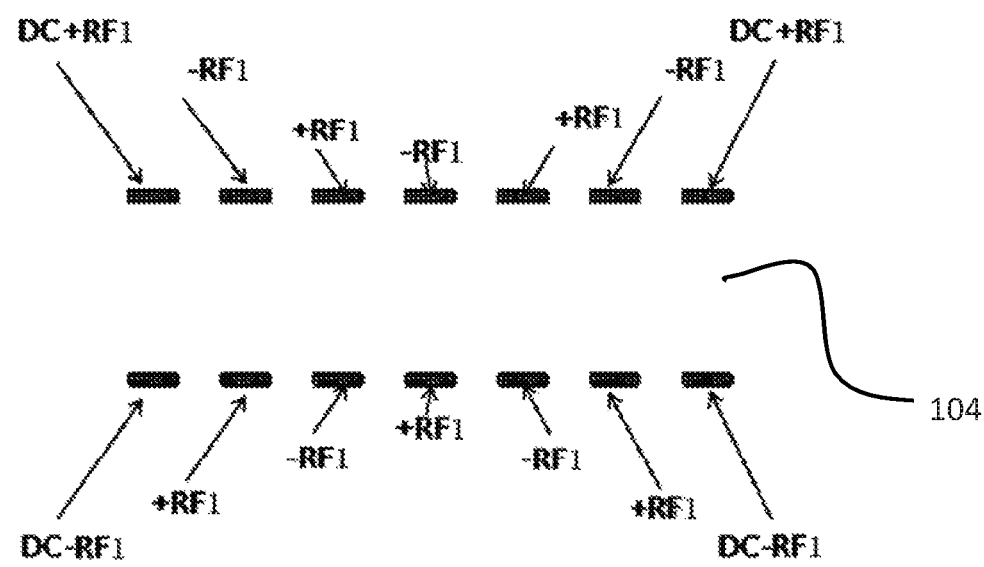
FIG. 2 shows a schematic view of a typical voltage applying mode of the ion guiding device of the present invention.
Figure 3:
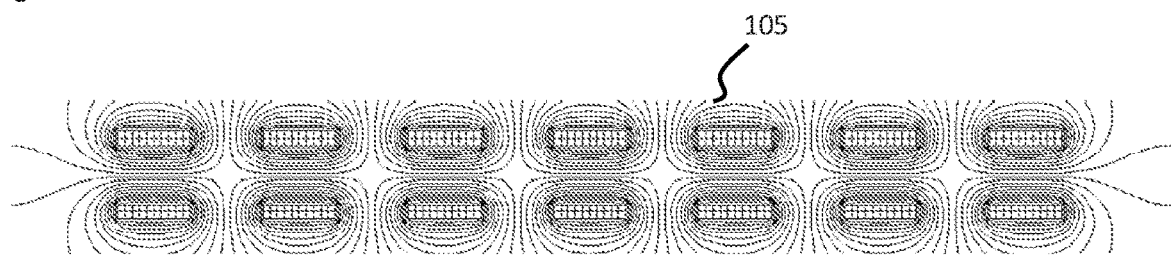
FIG. 3 shows a schematic structural view of approximate quadrupole-field ion channels formed at the ion outlet of the ion guiding device of the present invention.

Preferably, the operating gas pressure of the ion guiding device is in the range of one or more of $2 \times 10^5$ Pa-$2 \times 10^3$ Pa, $2 \times 10^3$ Pa-20 Pa, 20 Pa-2 Pa, 2 Pa-$2 \times 10^{-1}$ Pa, $2 \times 10^{-1}$ Pa-$2 \times 10^{-3}$ Pa and less than $2 \times 10^{-3}$ Pa. The optimal operating gas pressure of the ion guiding device 10 is in the range of 0.1 Pa-100 Pa. After ions are introduced to the ion inlet 104 via an upstream ion optical device, the ions collide with neutral gas such that a large amount of kinetic energy is lost and the ions are rapidly cooled. To reduce ion loss caused by free diffusion, as shown in FIG. 2, the first power supply device applies a group of radio-frequency voltages RF1 with opposite polarity on all electrodes 103 in the ion guiding device 10 such that a multipole field is formed in the vicinity of surfaces of the electrodes 103 to prevent ions from approaching the electrodes 103, thereby greatly reducing ion loss. Furthermore, for restricting the free diffusion of ions in a direction perpendicular to the space axis 102, as shown in FIG. 2, the second power supply device applies DC voltages on the electrodes 103 to establish a voltage barrier at both sides of the ion channel, thereby restricting the movement of the ions towards the both sides. Meanwhile, since the ion channel formed in the ion guiding device 10 along the space axis 102 has a cross section gradually reduced in a direction from the ion inlet 104 to the ion outlet 105, the axial electric potential intensity formed by penetration of the DC voltages applied on the electrodes 103 at both sides in the ion channel is also gradually reduced accordingly, i.e. an axial electric potential gradient along the space axis 102 is formed in the ion channel. The axial electric potential gradient is used for driving ions to transmit in a direction from the ion inlet 104 to the ion outlet 105 along the space axis 102. Meanwhile, the radius of a multipole field formed in the ion channel by radio-frequency voltages RF1 also gradually decreases along with a gradual decrease in the cross section of the ion channel, as shown in FIG. 3, and finally a plurality of ion outlets 105 with an approximate quadrupole-field distribution are gradually formed at the ion outlet.

Figure 4:
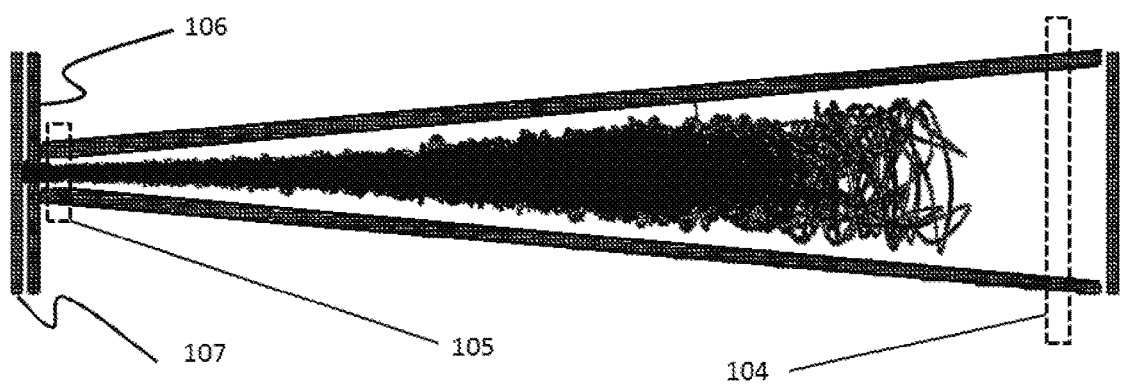
FIG. 4 shows a side view of ion trajectories in the ion guiding device of the present invention.
Figure 5:
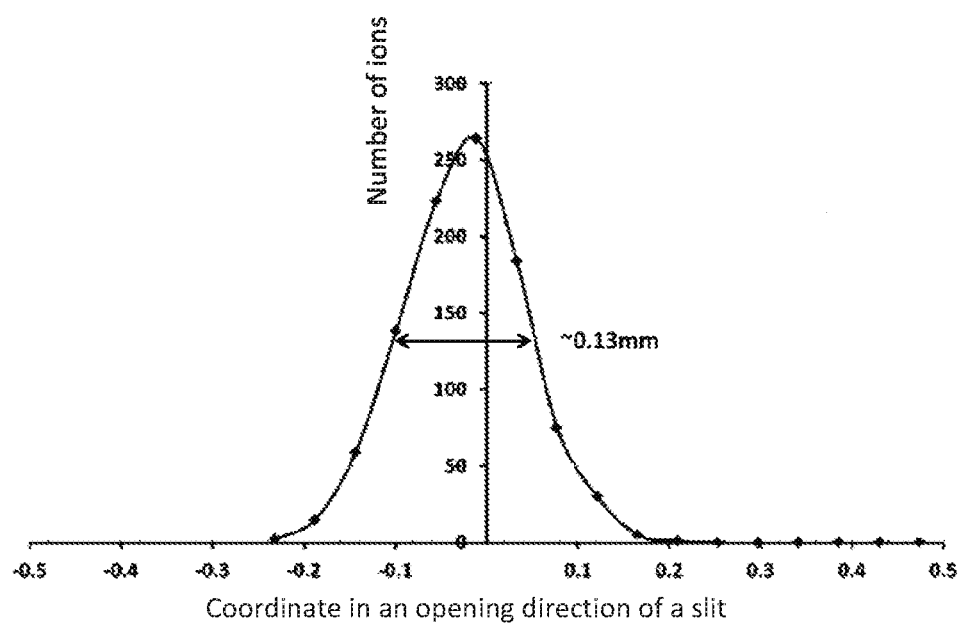
FIG. 5 shows a distribution graph of an ion beam in an opening direction of a slit which is detected on a detector in an ion simulation test of the present invention.

As shown in FIG. 4, during the transmission of ions, with a gradual decrease in the radius of a multipole field, ion trajectories are also gradually compressed to be thinner and thinner by a stronger and stronger multipole field. In an ion optical simulation, ions are extracted from an ion outlet 105 having a field radius of about 0.5 mm, then pass through a slit 106 having a 0.5 mm opening, and finally strike on a detector 107. An ion beam spot has a half-peak breadth of about 0.13 mm as detected in an opening direction of the slit 106, as shown in FIG. 5.

Figure 6:
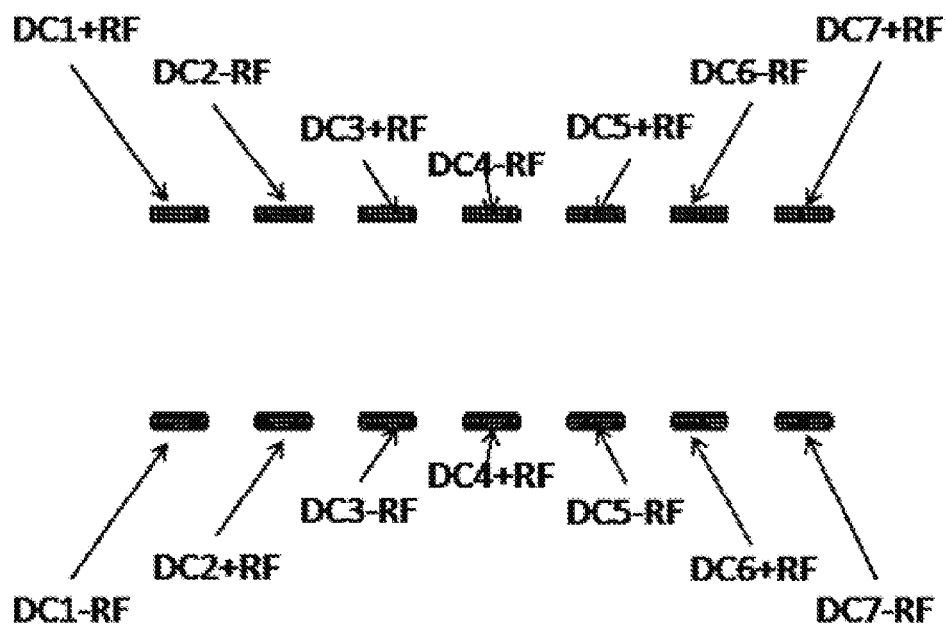
FIG. 6 shows a schematic view of a voltage applying mode of the ion guiding device when a transverse voltage distribution can be independently controlled in the present invention.
Figure 7:
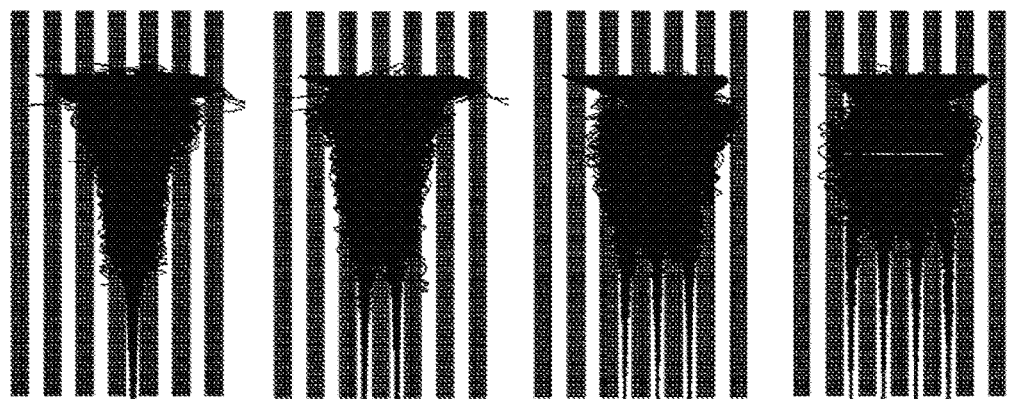
FIG. 7 shows a schematic view of ion trajectories obtained when ions select different ion channels during the adjustment of a transverse voltage distribution in the present invention.

In addition, for further flexibly controlling the transmission trajectories of ions, as shown in FIG. 6, an independently controllable DC voltage is respectively applied on all electrodes 103, thereby forming an independently controllable DC electric potential distribution in a transverse direction to restrict the selection of a transmission channel by ions. As shown in FIG. 7, the number and paths of ion channels can be freely selected by controlling a transverse DC electric potential distribution, thereby realizing the splitting effects of an ion beam. This is very favorable for reducing the space-charge effect, thereby enhancing the compression size of an ion beam and improving the dynamic range, etc.

In addition, the dwell time of ions can be changed by adjusting the intensity of a DC voltage so as to match the scanning speed of the entire instrument. In another operating mode of the embodiment, a DC power source may also be replaced with a square wave power source having an adjustable duty cycle, which can change the duty cycle to adjust the dwell time of ions on the one hand, and can also realize the bunching operation of an ion stream by using a square wave voltage on the other hand, thereby cutting a continuous ion stream into groups of ion packets and sequentially extracting the ion packets from the ion outlet 105. In addition, the time width of each ion packet can also be adjusted by changing the duty cycle of a square wave voltage so as to match the scanning speed of a subsequent-stage ion analysis device. Accordingly, for pulse-type ion analyzers such as a time-of-flight mass analyzer, an ion trap mass analyzer, an orbitrap mass analyzer and an ion drift tube which are coupled at a subsequent stage, the utilization efficiency of ions can be greatly improved such that these analyzers have a very high ion analyzing duty cycle. Another advantage of using a square wave power source also lies in that the flight path of ions can be prolonged at the same time of using a relatively short device length so as to achieve a higher ion collision-induced dissociation efficiency.

Furthermore, in another operating mode of the implementation structure, another group of radio-frequency voltages RF2 may be used instead of the above DC voltages, and then are applied on the electrodes 103 at both sides to restrict the movement of ions towards the both sides. Meanwhile, according to the pseudopotential theory, the radio-frequency voltages RF2 will penetrate in the ion guiding device to form an equivalent axial pseudopotential voltage distribution for driving axial transmission of ions. This operating mode is superior to the use of DC voltages in that, the radio-frequency voltages RF2 can form a radio-frequency focusing field in a radial direction of the ion channel, thus allowing ions to keep away from an electrode surface and converge towards the center. This can reduce the risk of striking on an electrode surface of ions to a certain extent. As is well known, an electric field formed by a DC voltage merely converges in a direction of both sides and diverges in a direction substantially perpendicular to an electrode surface, and the movement of ions towards an electrode surface is therefore intensified, which increases the risk of striking on an electrode surface of ions and therefore is adverse to lossless transmission of ions.

Figure 8:
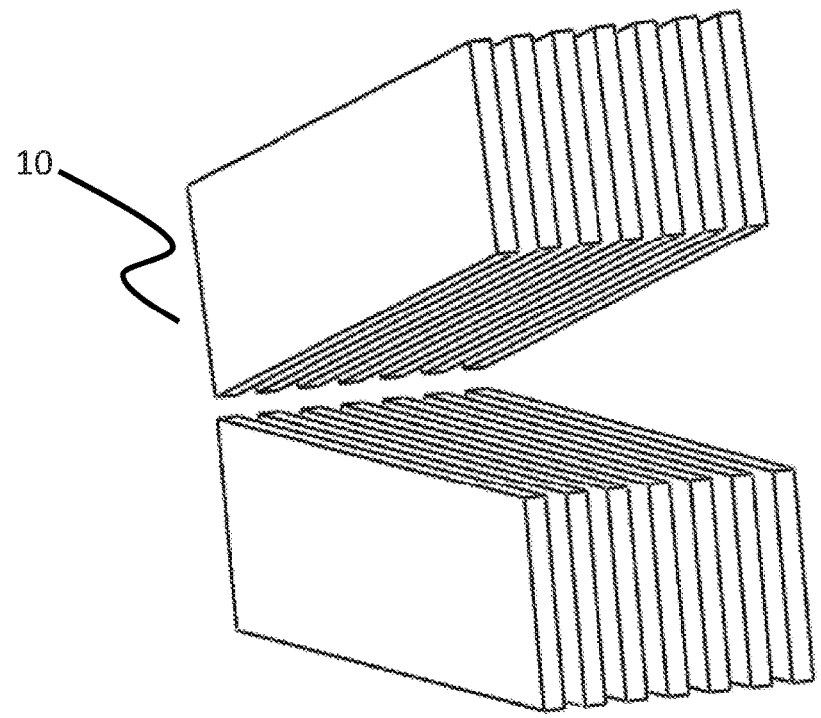
FIG. 8 shows a schematic structural view of the ion guiding device consisting of rectangular plate electrodes in the present invention.
Figure 9:
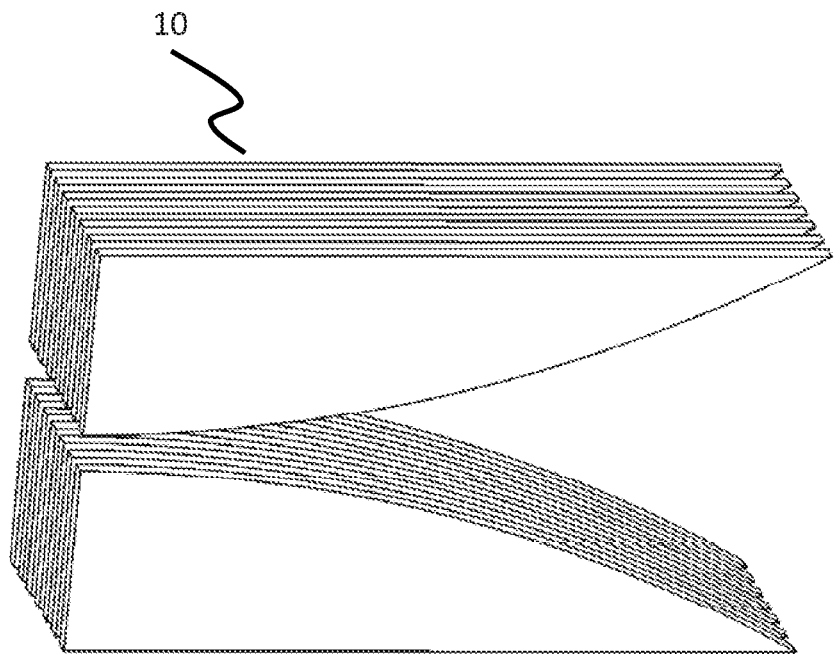
FIG. 9 shows a schematic structural view of the ion guiding device consisting of fan-shaped plate electrodes in the present invention.
Figure 10:
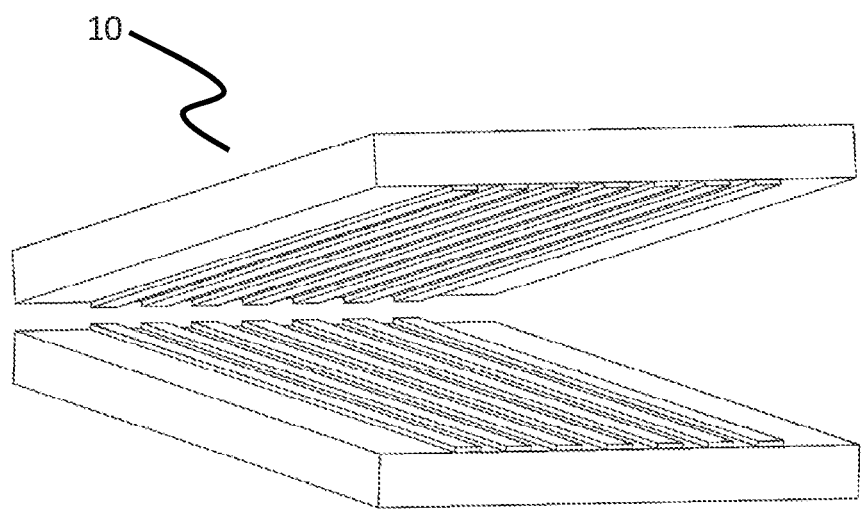
FIG. 10 shows a schematic structural view of the ion guiding device consisting of thin-layer plate electrodes based on an insulating substrate in the present invention.
Figure 11:
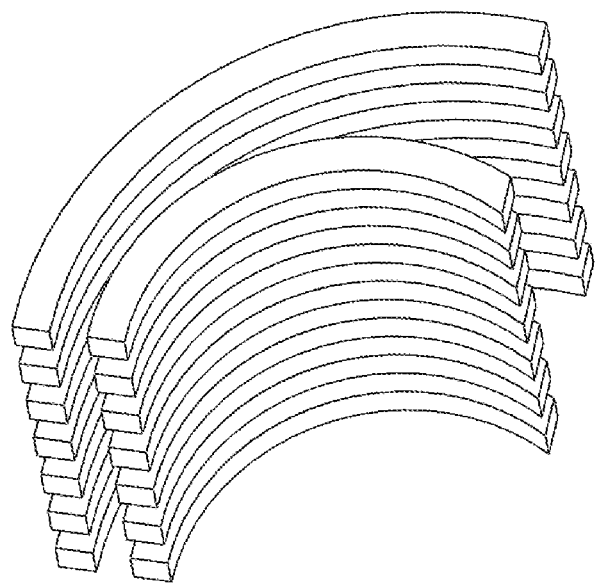
FIG. 11 shows a schematic structural view of the ion guiding device consisting of square-pole electrodes as a deflection structure at 90° in the present invention.
Figure 12:
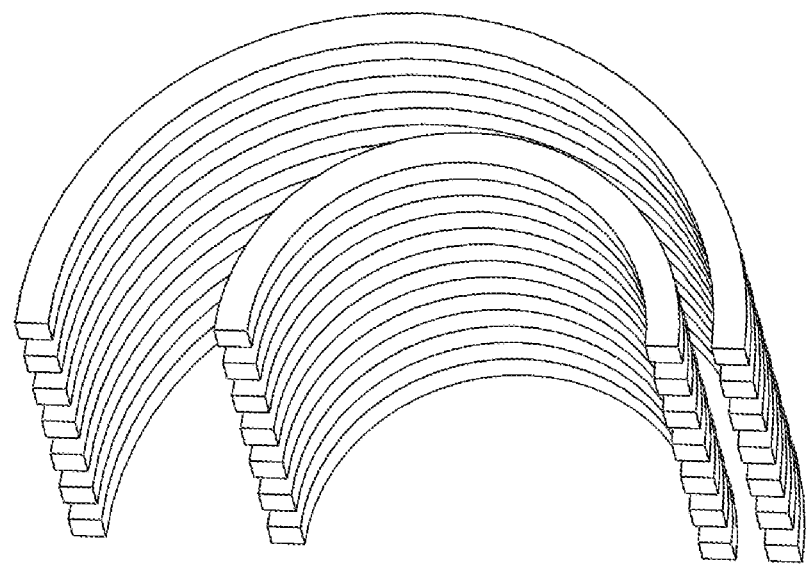
FIG. 12 shows a schematic structural view of the ion guiding device consisting of square-pole electrodes as a deflection structure at 180° in the present invention.

In other embodiments of the ion guiding device 10, the two sets of plate electrodes 101a and 101b may also be the forms as shown in FIGS. 8, 9 and 10. Any electrode form that can form a structure shown by the ion guiding device 10 without departing from the spirit of the present invention shall fall within the protection scope of the present invention. As shown in FIG. 9, a structure formed with a nonlinear contractive ion channel section from fan-shaped plate electrodes can further enhance the intensity of an axial penetration voltage, which is very favorable for reducing the dwell time of ions; and the structure has a larger ion inlet without increasing the electrode length, thus the acceptance area of ions can be greatly increased. As shown in FIG. 10, the two sets of thin-layer plate electrodes are adhered on an insulating substrate (e.g. by a printed circuit board technology, and other ways suitable for a plating process) to constitute the ion guiding device having the structure. The insulating substrate may be one of a printed circuit board, polyimide, ceramics and glass. This method is very suitable for machining an array electrode structure. An array electrode structure and some benefits thereof will be respectively illustrated below. As shown in FIGS. 11 and 12, square-pole electrodes may also be used to constitute the ion guiding device, which provides the advantage of greatly reducing the capacitance between the electrodes, thereby greatly reducing the requirements on the output power of a radio-frequency power source. The square-pole electrodes can constitute a deflection structure at various angles, e.g. a deflection structure at 90° in FIG. 11 and a deflection structure at 180° in FIG. 12.

It should be noted that not only plate electrodes but also nonplanar electrodes can be used for the two sets of electrodes 101a and 101b to realize their functions. The nonplanar electrodes may be electrodes whose surfaces are partially and/or all nonplanar.

Embodiment 2

Figure 13:
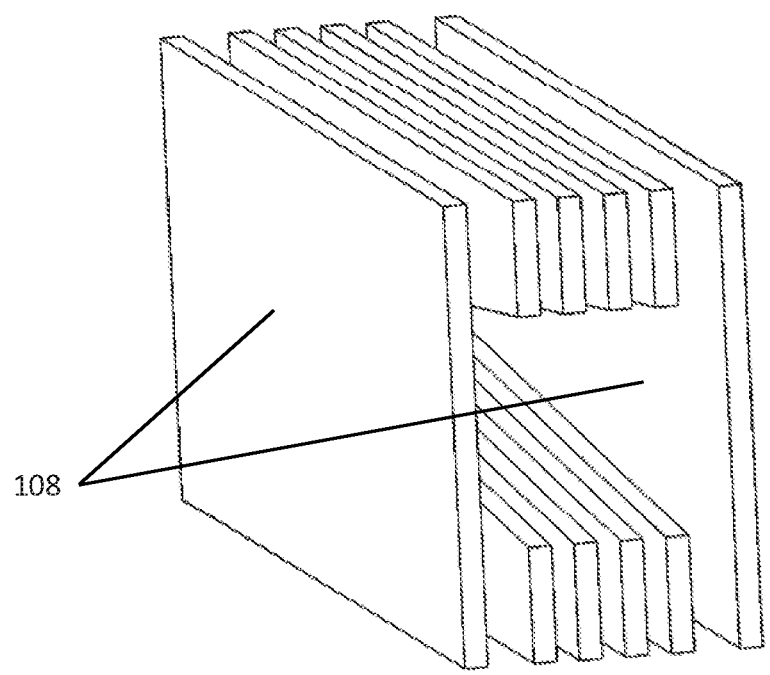
FIG. 13 shows a schematic structural view of the ion guiding device having auxiliary electrodes at both sides thereof in the present invention.
Figure 14:
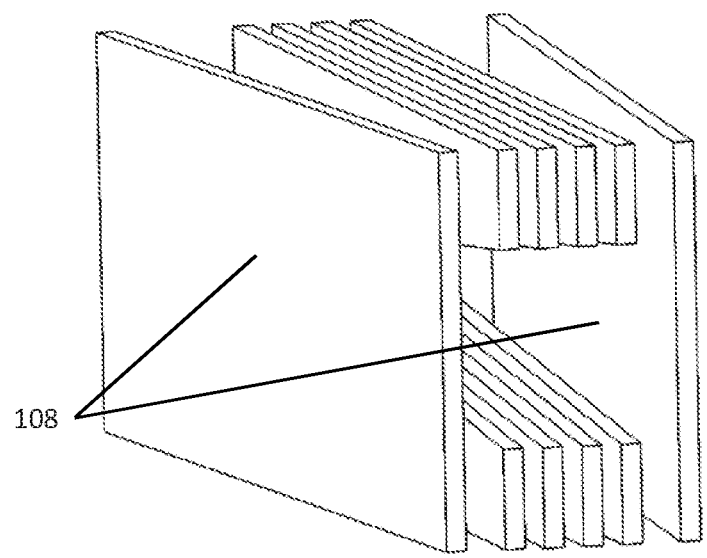
FIG. 14 shows a schematic structural view of the ion guiding device when the auxiliary electrodes at both sides thereof are not parallel to a space axis in the present invention.

FIG. 13 shows another embodiment of the ion guiding device of the present invention to further enhance the effects of an axial penetration electric potential gradient. In this structure, a set of auxiliary electrodes 108 are placed at both sides of the ion guiding device. The second power supply device applies voltage signals to the auxiliary electrodes. Voltages are applied on the auxiliary electrodes to restrict the movement of ions towards the both sides, and an axial penetration electric potential gradient is established in an ion channel to drive ion transmission. It should be noted that the second power supply device optionally applies voltage signals to the two sets of electrodes in the embodiment. This structure has the advantage that the auxiliary electrodes have a large coverage area, such that a stronger electric potential gradient can penetrate from the both sides to the inside of the ion guiding device, thus the dwell time of ions can be reduced. In addition, when the auxiliary electrodes 108 are not parallel to a space axis, and, as shown in FIG. 14, has a small distance at an ion inlet end and a large distance at an ion outlet end, a nonlinear electric potential gradient is formed in the ion guiding device, which can reduce the dwell time of ions in the ion channel. Meanwhile, the auxiliary electrodes 108 may be both planar and nonplanar electrodes. In addition, other forms of auxiliary electrode (including curved electrodes and the like) consistent with the concept of the present invention also shall fall within the protection scope of the present invention.

Embodiment 3

Figure 15:
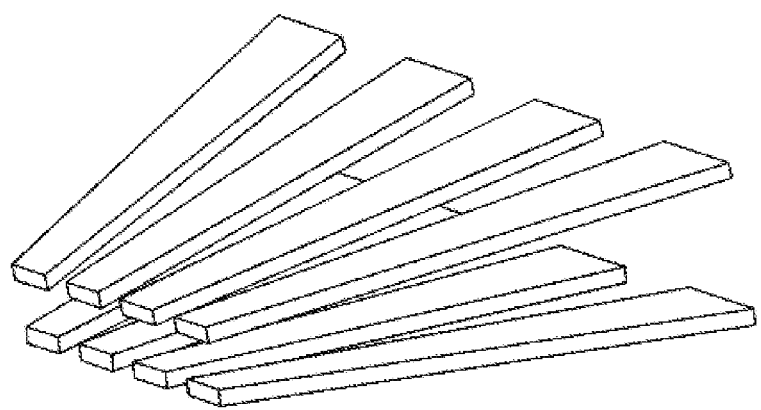
FIG. 15 shows a schematic structural view of the ion guiding device having a non-parallel structure in a transverse expansion direction in the present invention.

Different from the case that two sets of electrodes are in parallel expandable arrangement in a transverse direction as shown in FIG. 1, as shown in FIG. 15, another embodiment of the ion guiding device of the present invention further comprises a device having a non-parallel expandable arrangement structure in a transverse expansion direction. Electrode systems of the ion guiding device are not parallel structures in a transverse direction, but gradually come close together towards a central axis from an ion inlet. The embodiment has the advantages of using a relatively small number of electrodes while providing a large ion acceptance area as well as a small and centralized ion outlet. In addition, two sets of electrodes in the middle can substantially form a quadrupole rod structure having a gradually reduced field radius, thus it can also always maintain better ion focusing effects, especially at an area nearby the ion inlet, thereby reducing ion loss to a certain extent.

Embodiment 4

Figure 16A:
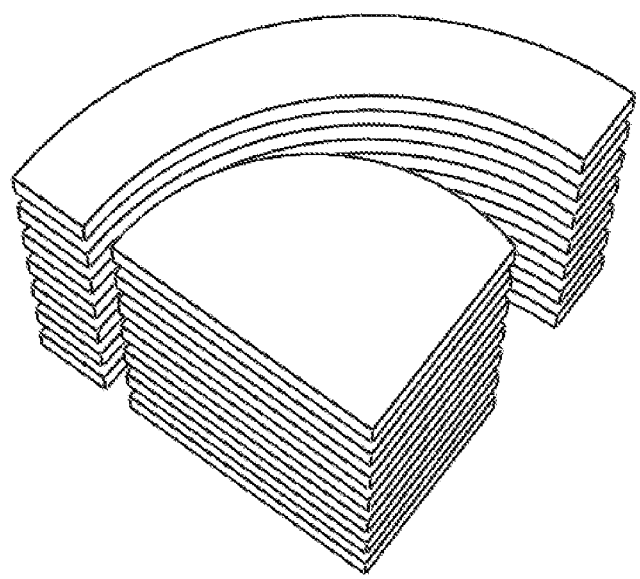
FIG. 16(a) shows a schematic structural view of an ion guiding device consisting of a space axis deflected along 90° in the present invention.
Figure 16B:
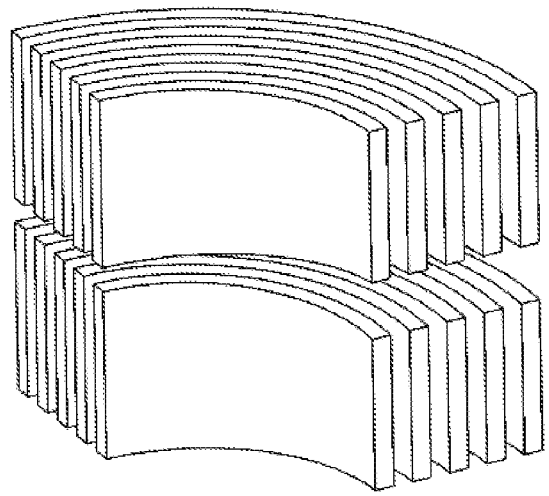
FIG. 16(b) shows a schematic structural view of another ion guiding device consisting of a space axis deflected along 90° in the present invention.
Figure 17A:
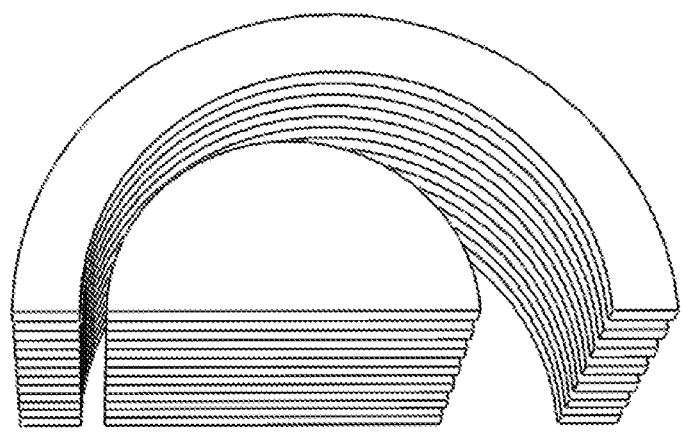
FIG. 17(a) shows a schematic structural view of an ion guiding device consisting of a space axis deflected along 180° in the present invention.
Figure 17B:
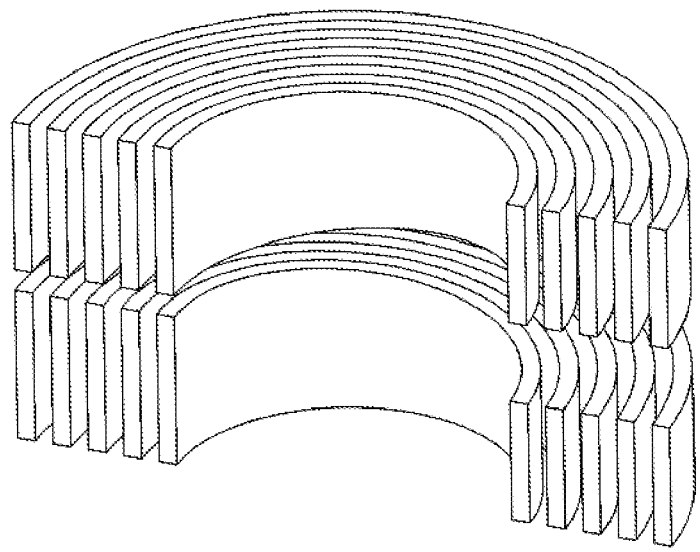
FIG. 17(b) shows a schematic structural view of another ion guiding device consisting of a space axis deflected along 180° in the present invention.
Figure 18:
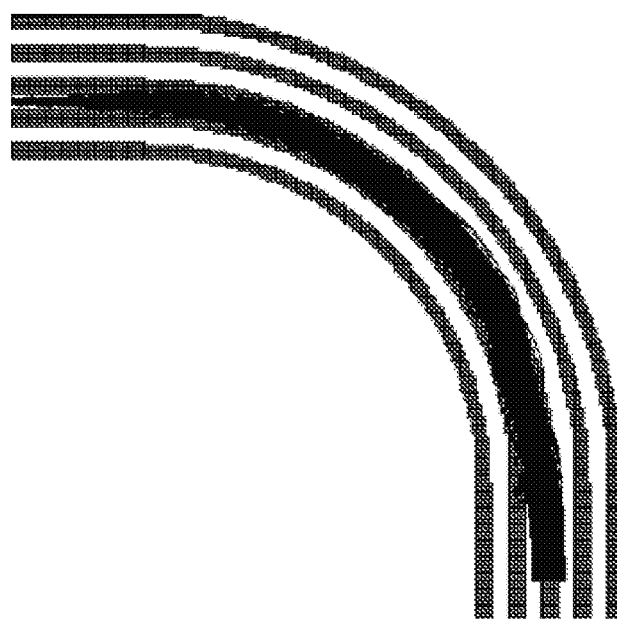
FIG. 18 shows a schematic view of ion deflection trajectories of ions in the ion guiding device consisting of a space axis deflected along 90° in an ion simulation of the present invention.

Different from the embodiment in which the space axis is a linear axis as shown in FIG. 1, other embodiments of the ion guiding device of the present invention further comprise a structure in which the space axis is a curved axis, e.g. an electrode structure in which the space axis is deflected at 90° as shown in FIG. 16(a) and FIG. 16(b) as well as an electrode structure in which the space axis is deflected at 180° as shown in FIG. 17(a) and FIG. 17(b). A voltage applying mode as well as basic forms of basic units of electrode systems in the embodiment is similar to those of the previously mentioned embodiments. The structure with a curved axis has the following advantages: the deflection of ion trajectories can be achieved, the interference from neutral gas molecules can be reduced by use of an off-axis structure on the one hand, and a more compact instrument design mechanism can be achieved on the other hand. FIG. 18 shows ion flight trajectories of ions in an electrode structure having a space axis deflected at 90° in an ion simulation experiment.

It should be noted that, when the space axis is a curved axis, an axial direction at the ion inlet is the first axial direction, an axial direction at the ion outlet is the second axial direction, and an included angle between the first axial direction and the second axial direction is one of less than 10°, 10°-20°, 20°-30°, 30°-40°, 40°-50°, 50°-60°, 60°-70°, 70°-80°, 80°-90°, 90°-100°, 100°-110°, 110°-120°, 120°-130°, 130°-140°, 140°-150°, 150°-160°, 160°-170° and 170°-180°.

Embodiment 5

Figure 19:
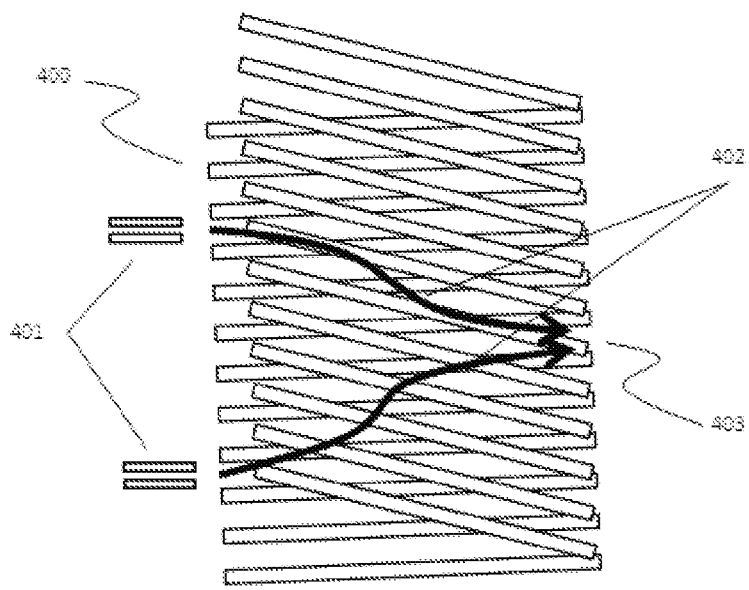
FIG. 19 shows a schematic view of an array electrode structure having a plurality of ion injection sources in the present invention.
Figure 20:
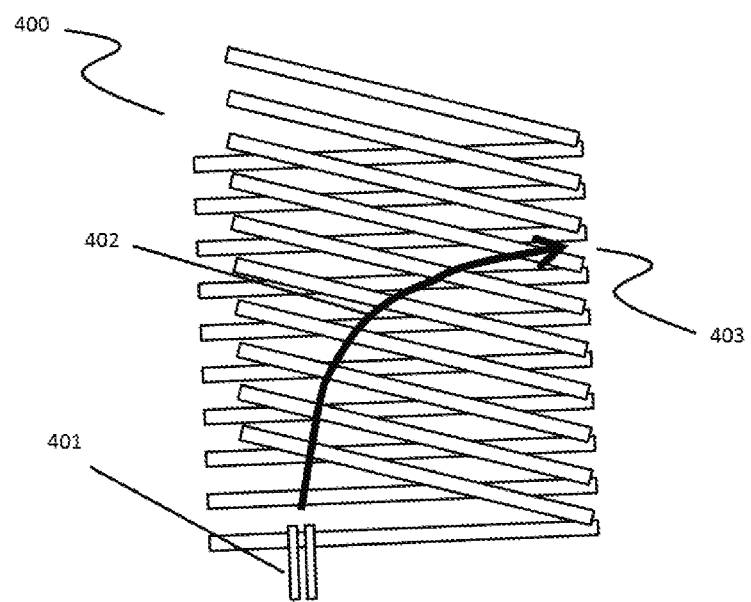
FIG. 20 shows a schematic view of an array electrode structure when ions are injected perpendicularly to a space axis in the present invention.

In other embodiments of the ion guiding device of the present invention, an electrode structure can also expand in a transverse direction to form an array-distributed electrode structure 400, as shown in FIG. 19. In the embodiment, an ion inlet end can receive ions from a plurality of ion injection ports 401 of a preceding-stage device. The ion injection direction is one or a combination of a direction of the space axis and a direction perpendicular to the space axis. FIG. 19 shows the injection of ions along a direction of the space axis. FIG. 20 shows the injection of ions along a direction perpendicular to the space axis.

As shown in FIG. 19, the arrangement of a transverse voltage distribution can allow an ion stream 402 to converge at the same ion outlet channel 403 and then be transmitted to the next stage. Because an electrode structure can arbitrarily expand in a transverse direction by using this method, a very large ion acceptance area is included. Meanwhile, the selection of an ion outlet channel by ions can be arbitrarily manipulated by flexibly designing a transverse voltage distribution. Accordingly, the array-distributed electrode structure 400 is very suitable for an instrument structure having a plurality of ion sources.

Figure 21:
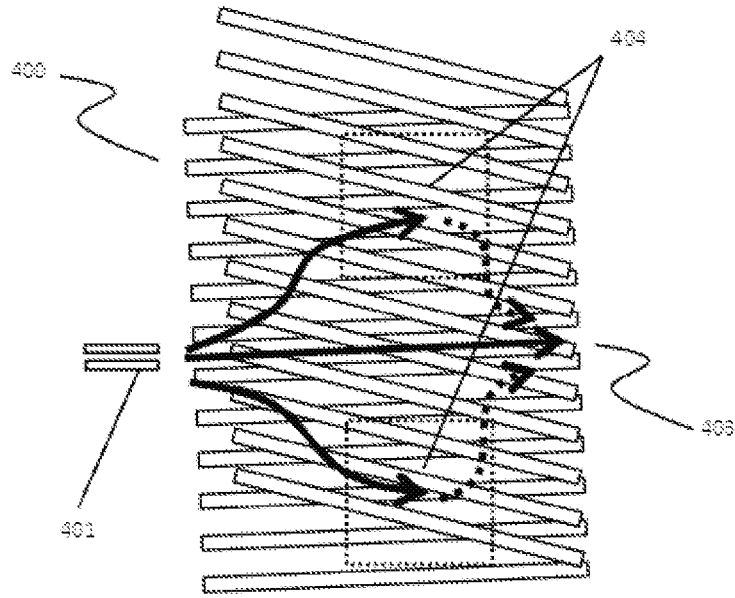
FIG. 21 shows a schematic view of an array electrode structure having an ion storage function in the present invention.
Figure 22:
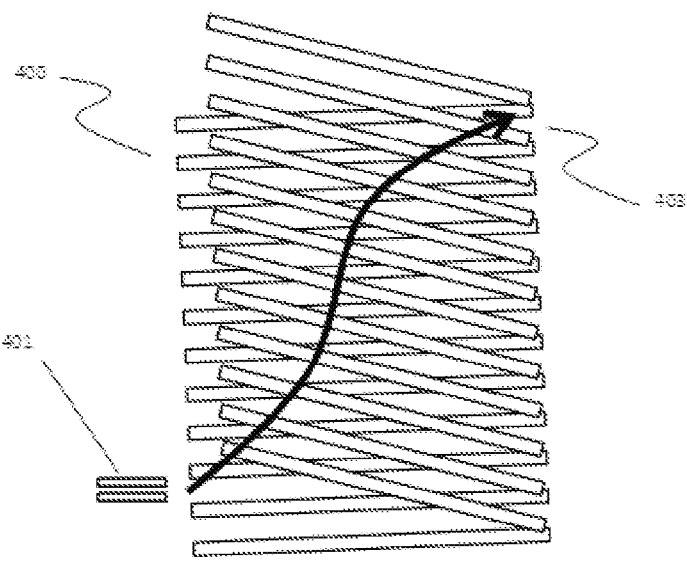
FIG. 22 shows a schematic view of an array electrode structure having an ion mobility analyzing function in the present invention.

Additionally, in other operating modes of the embodiment, a transverse voltage distribution can also be dynamically adjusted such that the array-distributed electrode structure has multiple ion manipulation functions, e.g. ion storage, ion mobility separation and measurement, etc. As shown in FIG. 21, when a low or zero transverse DC voltage gradient is applied at both sides of the array-distributed electrode structure 400, since an axial penetration driving voltage is not enough to counteract a pseudopotential barrier generated by a radio-frequency voltage, or in case of no axial driving voltage, ions will be accumulated in an ion storage area 404 at both sides. After the ions are accumulated for a certain period of time, the ions accumulated at both sides can return to a normal preset ion outlet channel 403 and then are transmitted and extracted to the next stage by changing a transverse voltage distribution at both sides. As shown in FIG. 22, the array-distributed electrode structure 400 may also be used as an ion mobility separation and measurement device in which ions injected from one side migrate to the other side under the action of a transverse electric potential gradient, and are continuously transmitted axially. Since an axial electric potential gradually cannot counteract a pseudopotential barrier generated by a radio-frequency voltage during drift, ions become stable in an axial direction such that the ions cannot escape axially. Once ions migrate to the other side, the axial penetration electric potential therein suddenly increases, thus the ions can be extracted axially from the ion outlet channel 403.

Figure 23:
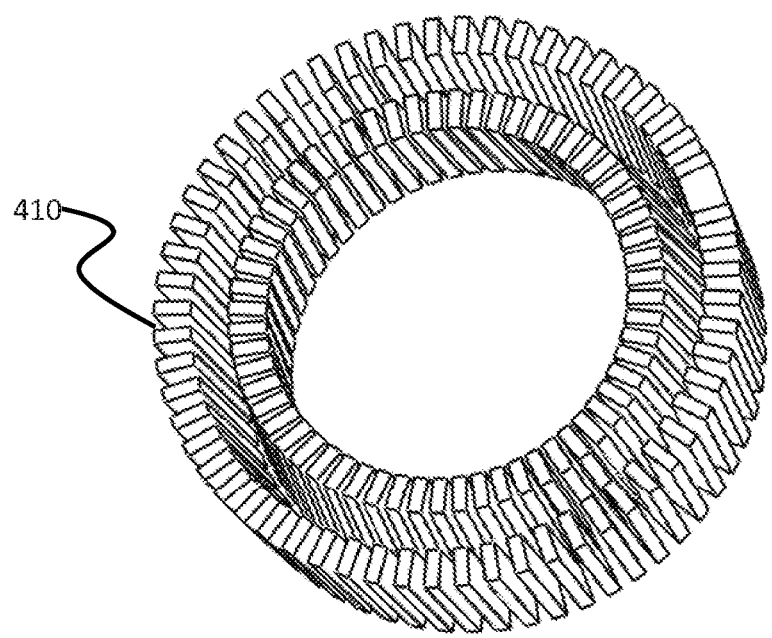
FIG. 23 shows a schematic view of a closed electrode array structure having an ion mobility analyzing function in the present invention.

Further, as shown in FIG. 23, the array-distributed electrode structure 400 can also constitute a closed electrode distribution array 410 along another closed curve. Ions can drift by more than one circle in the closed electrode array 410 along the closed curve by dynamically adjusting a voltage distribution on each electrode, thereby greatly increasing the drift distance of the ions and achieving a higher ion mobility resolution. Similar to the previously mentioned ion extraction modes, upon ion extraction, the axial penetration electric potential of a certain part of electrodes is increased sufficiently to counteract a pseudo-potential barrier generated by a radio-frequency voltage, thereby sequentially axially extracting ions from the ion outlet channel 403.

In summary, the ion guiding device of the present invention has the following advantages: the electrode shape and the device structure are simple, thereby facilitating machining, assembling and function expansion; efficient transmission and effective compression of ions can be realized; the device can be applied to relevant technical fields such as mass spectrometry and ion mobility spectrometry; the device can be applied to ion beam compression in an orthogonal-injection ion time-of-flight mass spectrometer, wherein ions are efficiently compressed to reduce the initial spatial distribution of the ions, thereby improving the resolution of the instrument; and in triple quadrupole mass spectrometers and other mass spectrometers, the device can conveniently realize off-axision optical design, which not only can effectively reduce the interference from neutral gas molecules and greatly improve the signal-to-noise ratio of the instrument, but also can reduce the volume of the instrument. Accordingly, the present invention effectively overcomes various disadvantages in the prior art and has a high industrial application value.

The above embodiments are only used for illustratively describing the principles and effects of the present invention, but are not intended to limit the present invention. Any persons skilled in the art can make modifications or changes to the above embodiments without departing from the spirit and scope of the present invention. Accordingly, all equivalent modifications or changes made by the persons having ordinary skill in the art without departing from the spirit and technical thought disclosed in the present invention still shall be covered by the claims of the present invention

What is claimed is:

1. An ion guiding device, comprising:
   two sets of electrodes extending along a space axis, a first power supply device and a second power supply device;

wherein the two sets of electrodes are expandably arranged along a first direction perpendicular to the space axis, at least one surface of each electrode in each set of electrodes is substantially on a same space plane, and said space planes for the two sets of electrodes are not same and not parallel and nonplanar, thereby forming an ion transmission channel having an ion inlet, an ion outlet, and a cross sectional area gradually reduced in a second direction perpendicular to the space axis and the first direction, and wherein the ion inlet of the ion transmission channel has a larger opening and the ion outlet thereof has a smaller opening;

wherein the first power supply device is used for applying radio-frequency voltages on at least a part of electrodes in only the two sets of electrodes to confine ions in the ion transmission channel in at least one direction perpendicular to the space axis; and wherein the second power supply device is used for applying voltage signals on at least a part of electrodes in only the two sets of electrodes to form a voltage distribution in at least one direction perpendicular to the space axis to control ion movement, and form a voltage distribution in a direction of the space axis to realize ion transmission along the space axis.

2. The ion guiding device according to claim 1, characterized in that: the space axis is a linear or curved axis.

3. The ion guiding device according to claim 2, characterized in that: when the space axis is a curved axis, an axial direction at the ion inlet is a first axial direction, an axial direction at the ion outlet is a second axial direction, and an included angle between the first axial direction and the second axial direction is one of less than 10°, 10°-20°, 20°-30°, 30°-40°, 40°-50°, 50°-60°, 60°-70°, 70°-80°, 80°-90°, 90°-100°, 100°-110°, 110°-120°, 120°-130°, 130°-140°, 140°-150°, 150°-160°, 160°-170° and 170°-180°.

4. The ion guiding device according to claim 1, characterized in that: electrodes in the two sets of plate electrodes are plate or nonplanar electrodes.

5. The ion guiding device according to claim 4, characterized in that: the plate electrodes comprise one or a combination of square-pole electrodes, rectangular plate electrodes, fan-shaped plate electrodes, and thin-layer plate electrodes adhered on an insulating substrate.

6. The ion guiding device according to claim 5, characterized in that: the insulating substrate is one of a printed circuit board, polyimide, ceramics and glass.

7. The ion guiding device according to claim 4, characterized in that: the nonplanar electrodes are electrodes whose surfaces are partially or all nonplanar.

8. The ion guiding device according to claim 1, characterized in that: an area ratio of the ion inlet to the ion outlet is one of 1-10, 10-100, 100-1,000 and more than 1,000.

9. The ion guiding device according to claim 1, characterized in that: the first power supply device sequentially applies radio-frequency voltages with opposite polarity to all electrodes in each set of electrodes.

10. The ion guiding device according to claim 1, characterized in that: voltage signals applied by the second power supply device are selected from one or a combination of DC voltages, square wave voltages, sawtooth wave voltages, triangle wave voltages and AC voltages.

11. The ion guiding device according to claim 10, characterized in that: a duty cycle of the square wave voltages is in the range of one or more of 0-10%, 10%-20%, 20%-40%, 40%-60% and 60%-100%.

12. The ion guiding device according to claim 10, characterized in that: the AC voltage signals have a frequency of 10 Hz -100 MHz.

13. The ion guiding device according to claim 1, characterized in that: the expandable arrangement of the two sets of electrodes in a direction perpendicular to the space axis is parallel and/or non-parallel expanded arrangement.

14. The ion guiding device according to claim 1, characterized in that: none of electrodes in the two sets of electrodes is segmented axially.

15. The ion guiding device according to claim 1, characterized by further comprising auxiliary electrodes, wherein the auxiliary electrodes are placed at both sides of the ion guiding device, and the second power supply device applies voltage signals to the auxiliary electrodes to restrict ion movement in a direction perpendicular to the space axis and produce an axial voltage gradient in the ion channel to realize ion transmission.

16. The ion guiding device according to claim 15, characterized in that: the auxiliary electrodes are parallel or not parallel to the space axis.

17. The ion guiding device according to claim 15, characterized in that: the auxiliary electrodes are planar or nonplanar electrodes.

18. The ion guiding device according to claim 1, characterized in that: the operating gas pressure of the ion guiding device is in the range of one or more of $2\times10^5$ Pa-$2\times10^3$ Pa, $2\times10^3$ Pa-20 Pa, 20 Pa-2 Pa, 2 Pa-$2\times10^{-1}$ Pa, $2\times10^{-1}$ Pa-$2\times10^{-3}$ Pa and less than $2\times10^{-3}$ Pa.

19. The ion guiding device according to claim 1, characterized in that: an optimal operating gas pressure of the ion guiding device is in the range of 0.1 Pa-100 Pa.

20. The ion guiding device according to claim 1, characterized in that: the two sets of electrodes expand along a direction perpendicular to the space axis to form an array structure.

21. The ion guiding device according to claim 1, characterized in that: the two sets of electrode systems expand along a closed curve to form a closed array structure.

22. The ion guiding device according to claim 1, characterized by comprising a plurality of ion injection ports for injecting ions into the ion inlet.

23. The ion guiding device according to claim 22, characterized in that: the ion injection direction is one or a combination of a direction of the space axis and a direction perpendicular to the space axis.

24. The ion guiding device according to claim 1, characterized in that: the ion guiding device serves as one or a combination of a preceding-stage ion guiding device, an ion mobility analysis device, an ion compression device, an ion storage device, a collision chamber and an ion buncher device of a mass spectrometer or an ion mobility spectrometer.

* * * * *